United States Patent [19]

Freebairn et al.

[11] 4,400,291

[45] Aug. 23, 1983

[54] ETHYLENE GAS GENERATING COMPOSITION

[75] Inventors: Hugh T. Freebairn, Brenham, Tex.; Tony L. Towns, Prattville, Ala.

[73] Assignee: Catalytic Generators, Inc., Norfolk, Va.

[21] Appl. No.: 229,754

[22] Filed: Jan. 29, 1981

[51] Int. Cl.$^3$ .......................... C07C 1/00; C09K 3/00
[52] U.S. Cl. .............................. 252/188.3 R; 426/263; 585/639
[58] Field of Search ................ 252/188.3 R; 426/263; 585/639

[56] References Cited

U.S. PATENT DOCUMENTS 3,780,127 12/1973 Young et al. ..................... 585/639
3,951,610 4/1976 Freebairn et al. ................ 585/639
4,270,015 5/1981 Knifton ........................... 585/639

FOREIGN PATENT DOCUMENTS 129874 11/1948 Australia ........................... 585/639

*Primary Examiner*—Irwin Gluck
*Attorney, Agent, or Firm*—Lalos, Leeds, Keegan, Lett & Marsh

[57] ABSTRACT

An ethylene gas generating liquid composition for catalytic conversion to ethylene. Ethanol is the primary ingredient of the liquid composition but there is also present 1.0% to 15% methanol, 0.1% to 10% of an ester such as amyl acetate and 0.1% to 15% of an aliphatic alcohol such as isopropanol. This liquid composition has been found to maintain a high conversion efficiency for the catalyst and minimizes the production of by-products.

11 Claims, No Drawings

ETHYLENE GAS GENERATING COMPOSITION

BACKGROUND OF THE INVENTION

This invention relates to an ethylene gas generating composition for use with a catalytic converter of the liquid composition to ethylene gas. The type of catalytic converter recommended is that disclosed in U.S. Pat. No. 3,951,610 issued to one of the co-inventor of this invention.

In the last few years the commercial market for ethylene gas has increased to include not only those uses for the initiation of the ripening of various fruits such as bananas, tomatoes, honeydews, pears, avocados or green citrus fruit such as oranges, lemons, grapefruits, limes and the like all of which has been set forth in the prior patent but also ethylene gas has been found to be useful in the curing of tobacco. This increased use has been in part directly resulting from the increased availability of the supply of ethylene gas in convenient form.

While there are still a number of commercial uses of ethylene gas for which the supply of ethylene is derived from the archaic steel cylinders containing pressurized ethylene, the gas generating apparatus disclosed for the first time as the catalytic converter in the prior patent has made a major contribution to the industry and has avoided the undersirable problems of unsafe storage and handling of the heavy steel cylinders of pressurized ethylene gas.

As described in the prior U.S. Pat. No. 3,951,610 the catalyst in the catalytic generator is preferably activated gamma alumina which theoretically produces in a mole for mole catalytic reaction ethylene by the dehydration of ethanol. Pure ethanol is the only reactive material capable of producing ethylene gas in this generator but ethanol alone is not a legal commercial substance saleable for use in catalytic generators of the type disclosed in the prior patent.

Ethanol is suitable for a number of well-known purposes the primary one, human consumption, makes it a government controlled substance. Therefore, the Bureau of Alcohol, Tobacco and Firearms of the Department of Treasury (BATF) in the United States does not permit the use of ethanol in the ethylene gas generating apparatus of the prior patent unless it has been previously sufficiently denatured to prevent practical separation and preclude potability.

BATF makes available an extensive list of denaturants in various combinations that would be acceptable to the government. Each of the previously known forms or combinations of denaturants generated various by-products such as diethyl ether and the like in the catalytic conversion. These substances were found to increase the flammability potential of the ethylene gas produced and could not be permitted to be released to the atmosphere with the ethylene in any undesirable quantity. The safe production of the ethylene gas in the generator was thus a critical factor. Efforts to improve the direction of the catalytic conversion reaction were unfortunately not successful without significantly reducing the efficiency of the catalyst as measured by the molar proportion of ethylene produced from the ethanol.

The liquid components suggested in the above prior patent for use in the gas generating apparatus were found to poison and contaminate the catalyst so that its efficiency for producing molar equivalent quantities of ethylene gas from ethanol is drastically reduced. Ultimately the catalyst must be replaced in the gas generating apparatus, a time consuming and expensive operation.

Ketones, for instance, were previously thought to be desirable components of the liquid gas generating composition and so were disclosed in the prior patent. It was discovered, however, that ketones such as acetone were a significant cause of the drop in efficiency in the catalytic production of ethylene. However simply omitting the offending denaturant was not a solution because the resulting composition would not be permitted by BATF to be sold commercially unless a denaturing substance acceptable to the government would be included.

The problem therefore surfaced how to meet the government requirements for a denatured liquid composition including primarily ethanol and yet neither poison the catalytic material effecting the generation of ethylene nor produce any harmful by-products through side reactions that would increase the flammability of the ethylene gas produced by the generator.

For instance it has been found that with various compositions dimethyl ether can be produced which would be an explosive hazard to the ethylene gas generated.

SUMMARY OF THE INVENTION

This invention relates to a liquid composition for use in a catalytic generator for the production of ethylene gas.

The liquid composition for catalytic conversion to ethylene gas includes on a volume basis 1.0% to 15% methanol, 0.1% to 10% of esters such as amyl acetate or ethyl acetate having not more than 10 carbon atoms and formed from a 5 carbon atom or less monocarboxylic acid and 0.1% to 15% of an aliphatic alcohol such as isopropanol having from 3 to 5 carbon atoms or an aliphatic hydrocarbon such as hexane or heptane having 5 to 9 carbon atoms and as the predominant ingredient ethanol.

OBJECTS OF THE PRESENT INVENTION

The present invention has a principal object the provision of a liquid composition for use in the catalytic conversion to ethylene gas.

An important object of the present invention is the provision of a liquid gas composition for the catalytic conversion to ethylene which minimizes undesirable by-products so as to avoid increased flammability of the ethylene gas generated.

Another important object of the present invention is the provision of a liquid composition for conversion by a catalyst to ethylene gas so as to maintain a high catalytic conversion efficiency of ethanol to ethylene and minimize the poisoning or decreased efficiency of the catalyst.

A further important object of the present invention is to avoid the production of hazardous by-products such as dimethyl ether when catalytically converting ethyl alcohol to ethylene.

DESCRIPTION OF THE PREFERRED EMBODIMENT

To avoid the precipitous drop in catalyst efficiency to approximately 40 to 70% of the theoretical due to the poisoning of the catalyst and the production of the various undesirable by-products, considerable research was conducted to develop an acceptable liquid gas generating composition. It was then discovered that several ingredients when added to the ethanol minimized the poisoning of the catalyst through the presence of denaturing compounds and avoided any undesirable level of the by-products of the catalytic reaction such as carbon monoxide or explosive by-products such as dimethyl ether. It was also determined that there was a synergism in the new components when combined with the ethanol.

It was discovered that one of the important ingredients to be combined with ethanol is methanol in a volume proportion of 1% to 15% in the broadest aspects preferably a maximum of 10% and most preferably a maximum of 5% by volume of the total composition. Methanol was found to enhance the effectiveness of the composition.

The second ingredient found to be important to be combined with the ethanol is an ester having not more than 10 carbon atoms and formed from a monocarboxylic acid of not greater than 5 carbon atoms. The esters found particularly useful are amyl acetate and ethyl acetate alone or in combination. Of these two, it has been discovered that amyl acetate is a significant and unexpected improvement in producing the maximum amount of ethylene gas for the longest period of time using the same catalyst compared to the incorporation of ethyl acetate. The proportions of the esters in the broadest aspects of the present invention are 0.1% to 10% preferably 0.1% to 5% and most preferably 0.5% to 2% by volume. Due to its demonstrated superiority the amount of amyl acetate to be used may be less than that of the other esters. Surprisingly, the use of methanol further enhanced the effectiveness of the esters and particularly the acetates.

The remaining additive to be used in the liquid composition for the catalytic production of ethylene is an aliphatic alcohol having 3 to 5 carbon atoms such as isopropanol, butanol and pentanol. It is also possible although considerably less desirable in an economic sense to utilize an aliphatic hydrocarbon having 5 to 9 carbon atoms such as pentane, hexane, heptane, octane or nonane. The proportions of the aliphatic alcohol or aliphatic hydrocarbon are 0.1% to 15% and preferably 1% to 10% and most preferably 1% to 5%.

SPECIFIC EXAMPLE

In specific tests using the catalytic generator of U.S. Pat. No. 3,951,610 the following liquid composition was poured into the generator:
ethanol—87 ml
methanol—4 ml
isopropanol—5 ml
ethyl acetate—3 ml
amyl acetate—1 ml The catalytic efficiency of the generator was determined to be 82.3% based upon the molar proportion of the ethylene produced compared to the ethanol input. Several months of use did not destroy the effectiveness of the catalytic reaction as compared to the prior art compositions disclosed in U.S. Pat. No. 3,951,610 wherein the inclusion of acetones or other ketones and the absence of use of methanol severely damaged the catalyst after a far lesser volume of liquid composition had been poured into the generator.

It also has been learned that the use of the present invention in the patented catalytic generator minimizes the production of the tar and resins representative of some of the by-products produced by the side reactions compared to any legally denatured ethanol containing composition. Lowered production of the tar and resin by-products extends the life of the catalyst and permits the maintenance of a high conversion efficiency.

The present invention has also substantially eliminated the production of hazardous and explosive by-products such as dimethyl ether and further avoided carbon monoxide in noxious quantities.

It should be apparent that the stated objects of this invention have been attained by this novel liquid composition and therefore the scope of the invention should be limited solely by the appended claims.

We claim:

1. A liquid composition for the catalytic conversion to ethylene comprising, by volume,
   (a) 1.0% to 15% methanol,
   (b) 0.1% to 10% of an ester having not more than 10 carbon atoms and formed from a monocarboxylic acid of not greater than 5 carbon atoms,
   (c) 0.1% to 15% of a compound selected from the group consisting of an aliphatic alcohol having from 3 to 5 carbon atoms and an aliphatic hydrocarbon having 5 to 9 carbon atoms and
   (d) ethanol.

2. The composition of claim 1 including,
said methanol being up to 10% by volume.

3. The composition of claim 1 including,
said aliphatic alcohol and said aliphatic hydrocarbon be present in the amount up to 10% by volume.

4. The composition of claim 1, 2 or 3 including,
said esters being present in the amount up to 5%.

5. The composition of claim 1 including,
said methanol being up to 10% by volume,
said aliphatic alcohol and said aliphatic hydrocarbon being present in the amount up to 10% by volume, and
said esters being present in the amount up to 5%.

6. The composition of claim 1 including,
said methanol being present up to 5% by volume.

7. The composition of claim 1 including,
said aliphatic alcohol and said aliphatic hydrocarbon being present in the amount up to 5% by volume.

8. The composition of claim 1, 6 or 7 including,
said esters being present in the amount up to 0.5% to 2%.

9. The composition of claim 1 including,
said methanol being up to 5% by volume,
said aliphatic alcohol and said aliphatic hydrocarbon being present in the amount up to 5% by volume, and
said esters being present in the amount up to 0.5% to 2%.

10. The composition of claim 1 including,
said esters are selected from the group consisting of amyl acetate and ethyl acetate.

11. The composition of claim 1, 3, 5, 7, or 9 including,
said ester in amyl acetate and said aliphatic alcohol is isopropyl alcohol.

* * * * *